United States Patent
Araya Brenes

(10) Patent No.: US 10,106,478 B2
(45) Date of Patent: Oct. 23, 2018

(54) PROCESS FOR PRODUCING A MULTIFUNCTIONAL PRODUCT AND THE DEVICE FOR APPLYING SAID PROCESS

(71) Applicant: Blueplasma Power, S.L., Castellón (ES)

(72) Inventor: Mario Araya Brenes, Castellón (ES)

(73) Assignee: BLUEPLASMA POWER, S.L., Castellön (ES)

( * ) Notice: Subject to any disclaimer, the term of this patent is extended or adjusted under 35 U.S.C. 154(b) by 0 days.

(21) Appl. No.: 15/487,510

(22) Filed: Apr. 14, 2017

(65) Prior Publication Data
US 2017/0297989 A1    Oct. 19, 2017

(30) Foreign Application Priority Data

Apr. 15, 2016   (ES) .................................. 201630473

(51) Int. Cl.
| | |
|---|---|
| *B01D 3/00* | (2006.01) |
| *B01J 8/00* | (2006.01) |
| *C07C 45/38* | (2006.01) |
| *C07C 41/01* | (2006.01) |
| *B01J 8/06* | (2006.01) |
| *C07C 29/154* | (2006.01) |
| *C07C 45/37* | (2006.01) |
| *C07C 41/09* | (2006.01) |
| *C07C 41/56* | (2006.01) |
| *C10L 1/02* | (2006.01) |
| *C10L 1/185* | (2006.01) |
| *C10L 1/198* | (2006.01) |
| *C10L 10/06* | (2006.01) |

(52) U.S. Cl.
CPC ............. *C07C 45/38* (2013.01); *B01D 3/009* (2013.01); *B01J 8/067* (2013.01); *C07C 29/154* (2013.01); *C07C 41/01* (2013.01); *C07C 41/09* (2013.01); *C07C 41/56* (2013.01); *C07C 45/37* (2013.01); *C10L 1/026* (2013.01); *C10L 1/1852* (2013.01); *C10L 1/1985* (2013.01); *C10L 10/06* (2013.01); *B01J 2208/00017* (2013.01); *B01J 2208/00044* (2013.01); *B01J 2208/00539* (2013.01); *B01J 2208/00548* (2013.01)

(58) Field of Classification Search
CPC ......... C07C 45/38; C07C 41/01; B01D 3/009; B01J 8/67
USPC .................................................. 568/475, 613
See application file for complete search history.

(56) References Cited

U.S. PATENT DOCUMENTS

| 6,166,266 A | 12/2000 | Hagen et al. |
| 2005/0154226 A1 | 7/2005 | Liu et al. |
| 2008/0216390 A1 | 9/2008 | Tebben et al. |

FOREIGN PATENT DOCUMENTS

EP      0038138 A1   10/1981

OTHER PUBLICATIONS

Spanish Search Report and Written Opinion dated Jan. 23, 2017 issued in connection with 201630473; 6 pgs.

*Primary Examiner* — Sikarl A Witherspoon
(74) *Attorney, Agent, or Firm* — Vedder Price, P.C.

(57) ABSTRACT

A process by which the raw material, a gas comprising mainly hydrogen, carbon monoxide and carbon dioxide, is introduced into a first reactor together with a catalyst, in which one or more reactions take place that produce methanol or dimethyl ether or both, which are then introduced into a second reactor adding oxygen and a catalyst and producing formaldehyde and a minority of dimethyl ether, and where there may be an excess of water, such water being extracted from the process and the remaining products being introduced into the third reactor with, optionally, an additive, and such raw material is exposed to catalysts and under an atmosphere at medium temperature and pressure, in order to produce three or four groups of chemical reactions that, after extracting most of the water that is generated as a residue during the process, produces as a result a liquid multifunctional product that can be used as a solvent, a foaming agent or an oxygenated fuel; said product, normally a fluid, comprises polyoxymethylene dimethyl ethers with molecular formula $CH_3O(CH_2O)_nCH_3$ wherein n has a value between 1 and 7.

8 Claims, 1 Drawing Sheet

DIBUJOS
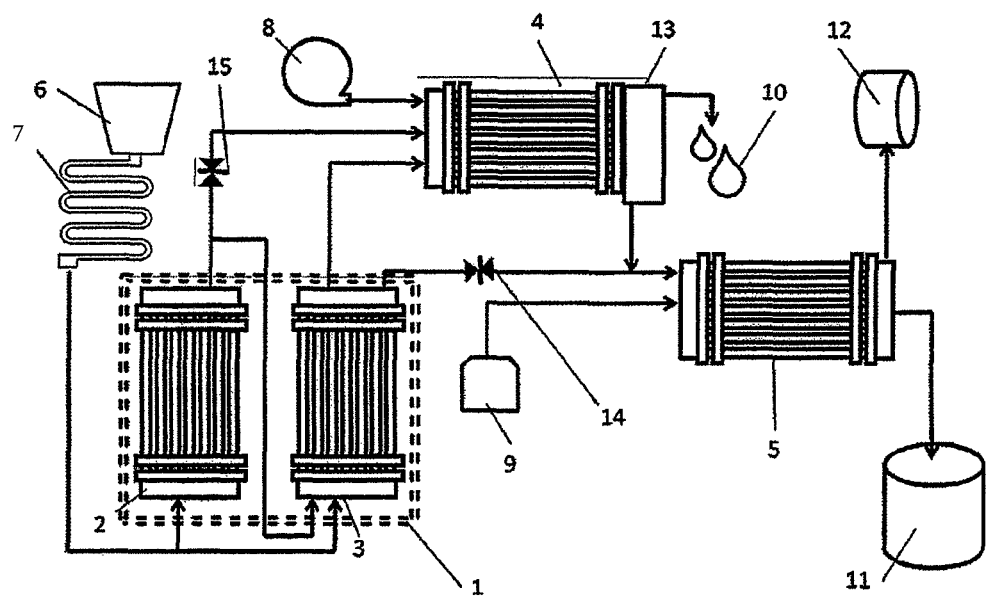

PROCESS FOR PRODUCING A MULTIFUNCTIONAL PRODUCT AND THE DEVICE FOR APPLYING SAID PROCESS

CROSS-REFERENCE TO RELATED APPLICATIONS

This application claims the benefit of and priority from Spain Application No. P 201630473, filed Apr. 15, 2016, which is wholly incorporated herein by reference.

The invention comprises: A) a process for obtaining a multifunctional product from raw material comprising oxygen, a synthesis gas and an optional additive, B) a device for applying the intended process, comprising at least three reactors in sequence wherein a maximum of four and a minimum of three groups of reactions occur, and C) the product finally obtained through this process.

During the procedure, the raw material that is introduced into a first reactor comprises a synthesis gas that mainly contains carbon monoxide and hydrogen, the raw material that is introduced into a second reactor comprises mainly oxygen, and the raw material that is introduced into a third reactor comprises an optional additive, and these are exposed to catalysts under an atmosphere at medium temperature and pressure, so that three or four groups of chemical reactions occur that, after extracting most of the water generated as a residue during the process, produces as a result a multifunctional liquid product that may be used as a solvent, a foaming agent or an oxygenated fuel; said product, normally a fluid, comprises polyoxymethylene dimethyl ethers with molecular formula $CH_3O(CH_2O)_nCH_3$ wherein n has a value between 1 and 7.

This product that is obtained, along with its by-products that are also liquid at room temperature and atmospheric pressure, such as methanol, and water traces amongst others, shall from now on be called the multifunctional product. The fraction that corresponds to its byproducts may be reduced via a fractional distillation and its chemical stability may also be improved by modifying its pH by incorporating an optional additive in the last group of reactions.

BACKGROUND

The cheapest conventional systems for converting the synthesis gas into a product with similar features to those of the multifunctional product of this patent are via the by-products of the synthesis gas itself: via methanol and formaldehyde or via dimethyl ether and formaldehyde.

The first route for producing a product similar to the multifunctional product of this patent requires first converting the synthesis gas to methanol at pressure of approximately 60 bar and a temperature of approximately 250° C., passing it several times through the same reactor since the water generated in the process limits conversion of the synthesis gas to methanol. This modern process of producing low pressure methanol was developed in late 1960.

After producing the methanol, it must be processed in a separate reactor and at a pressure close to atmospheric pressure, so that it becomes dissociated into formaldehyde and hydrogen at a temperature of approximately 600° C. using copper or silver as a catalyst, or instead oxidized with air to convert it to formaldehyde and water at 280° C. using a pressure close to the atmospheric pressure.

Finally, the formaldehyde produced is made to react with methanol, increasing the pressure of the latter to 20 bar at an approximate temperature of 250° C. in a reactive distillation process, using ionic exchange resin as an acid catalyst and thus producing a product with similar features to the multifunctional product.

An example of this process is U.S. Pat. No. 6,160,186 by BP/AMOCO. However, this process loses efficiency when the synthesis gas, due to the production of water during methanol production, generates a low percentage of conversion to methanol and therefore requires several passes through the reactor under a pressure of approximately 60 bar, and after each passage this methanol needs to lose pressure and cool down so that the water generated in the process can be extracted from it, since this acts as a limiter in the conversion; for the above-mentioned separation, a distillation process called flash distillation is generally used, which is performed at a lower temperature and pressure than is required for methanol synthesis.

Then, in order to convert it to formaldehyde, the methanol must be reheated, generally in the presence of an oxidizing agent such as air, oxygen, water or CO2 and a suitable catalyst. Once the methanol has oxidized to formaldehyde, it must be cooled down and stored in a stock that is separate from the process line. In order to later recover it from this stock it must be heated and injected at the same time as the methanol, at an approximate pressure of 20 bar and a temperature of close to 180° C. so that said products can react in a process known as reactive distillation using an ion exchange resin as a catalyst.

Another known route for producing a similar product to the multifunctional product is from a synthesis of gas and oxygen. It is less conventional than the first route but produces a majority conversion, and this is converting the synthesis gas directly to dimethyl ether at a temperature of close to 250° C. and at medium pressure: from 20 to 40 bar. It is then stored in a container at moderate pressures and ambient temperature, where it is extracted in order to be combined with formaldehyde taken from a source that contains or generates it, in order to finally process both products, dimethyl ether and formaldehyde, by heating them to a temperature of approximately 180° C. and subjecting them to a pressure of about 20 bar using ion exchange resin as a catalyst.

This process requires producing the formaldehyde, generally obtained from methanol, with the drawbacks indicated for the first route, or taking it from other products that already contain the aldehyde but are more expensive; or in the pure form, such as is the case for trioxane, paraformaldehyde and formaldehyde in solution with methanol or water. This last route for obtaining formaldehyde in order to produce polyoxyethylene dimethyl ether is used in the process developed by BASF and disclosed in U.S. Pat. No. 7,999,140 B2.

The multifunctional product subject matter of this patent is useful as a solvent and also as a liquid fuel due to its features and advantages, amongst which we can highlight:

1. It has low toxicity.
2. It can be mixed in all proportions with petrol or diesel.
3. When the objective is to mix it with diesel, it can be adjusted to a different degree of viscosity and a different cetane number.
4. It keeps in a single liquid phase mixtures of alcohol with hydrocarbons such as petrol or diesel, even when there is contamination with water.
5. When it is mixed and combusted with hydrocarbons it lowers the toxic levels of the gas emissions from combustion of the hydrocarbon.
6. It can be obtained from biomass or hydrocarbons.
7. It is biodegradable.

8. It acts as a carbon dioxide sink since it generates less CO2 per net unit of energy obtained and due to its oxygen content being greater than 50% when used as a component in conventional fuels, with an irrelevant negative impact on the power of the engine used.
9. It allows being complemented with other fuel components so as to use up to 100% in conventional engines without substantial modifications and obtaining a competitive efficiency with respect to conventional fuels.
10. It cleans the soot and water from fuel tanks and injectors.
11. It works with the current pumping systems at petrol stations.

In the current state of science there is no integrated process that allows obtaining the multifunctional product only from synthesis gas, oxygen and an optional additive, using the integration of known technologies, so that when they interact they are capable of generating a surprising synergy characterized in that it:

1. Achieves a majority percentage of conversion to the multifunctional product in a single pass.
2. Is capable of maintaining the process going as a self-heating and continuous reaction at the expense of the heat energy received from the partial oxidation of part of its raw materials and without causing a great consumption of electric power, using almost all of it to keep the process at a moderate pressure.
3. Prevents the need for storing the intermediate products of the process externally to the process line.
4. Produces a multifunctional product that, adequately applying the optional additive, can change its pH and thus its physical and chemical characteristics so that, on the one hand, in the presence of acid substances, it prevents the inversion of the reactions that produced it; and on the other hand, when it is used as a fuel, it increases its sensitivity to detonation.

The four points above are precisely what is achieved with the process and device disclosed in this patent and described below.

DESCRIPTION OF THE INVENTION

The invention relates to a process for obtaining a multifunctional product from a raw material comprising oxygen, synthesis gas, and an optional additive, and also relates to the device for applying said process and also to the product finally obtained with said process.

1. Regarding the Process

Regarding the process, we can indicate that it is globally exothermic, since, although it comprises some endothermic reactions, the exothermic reactions release more heat energy than what the endothermic reactions consume. So that the endothermic reactions can stay at the required temperature, this process comprises reusing the heat released by the exothermic reactions.

The process is thus self-heating, without requiring external sources to provide more heat other than that used a single time to start the process, and with respect to electric power, its use is required to maintain constant pressure of the synthesis gas.

The process comprises at least three groups of reactions and a maximum of four groups of reactions.

To achieve this, the device that is part of this patent comprises at least three reactors in sequence: a first reactor, that may comprise in turn a main reactor and an auxiliary reactor, in which at least one of the two first groups of reactions takes place, a second reactor in which the third group of reactions takes place, and a third reactor in which the fourth group of reactions takes place.

Before the start of the process itself, the raw material is primed to a temperature of between 200° and 300° C. and to a pressure between 18 and 60 bar, preferably close to 40 bar, since the raw material is a gas comprising mainly:
a. Hydrogen
b. Carbon monoxide
c. Carbon dioxide.

In a first phase, in the first reactor, which comprises in turn the main reactor and optionally an auxiliary reactor, at least one of the first two groups of reactions described below occurs.

The synthesis gas consisting mainly of hydrogen and carbon monoxide enters the first reactor at a temperature of between 200 and 300° C. and at a pressure between 20 and 60 bar, preferably 40 bar, and comes in contact with at least one catalyst.

Depending on the composition of this catalyst, the reactions of the first group to produce methanol or those of the second group to produce dimethyl ether can be triggered.

If the catalyst is for producing methanol, the preferred compound is based on $CuO/ZnO/Al_2O_3$, which we shall call C1, which accelerates the main reaction of the first group: $CO+2H_2 \rightarrow CH_3OH$.

If the catalyst is for producing dimethyl ether, the preferred compound is based on $CuO/ZnO/Al_2O_3$ and aluminum oxide, which we shall call C2 and which accelerates the main reaction of the second group: $3CO+3H_2 \rightarrow CH_3OCH_3+CO_2$.

When the two first groups of reactions occur simultaneously during the process, the catalysts corresponding to each one of these two groups of reactions can be arranged in sequence, either in parallel or both mixed in any proportion, and the following reaction takes place: $2CH_3OH \rightarrow CH_3OCH_3+H_2O$, and the residual water from this reaction is used as a raw material to form more hydrogen via the side reaction: $CO+H_2O \rightarrow CO_2+H_2$, thus avoiding having an excess of water among the reagents, which means reducing the main limiter in the conversion of the synthesis gas to dimethyl ether and methanol.

As stated above, the first reagent may comprise a main reagent and an auxiliary one.

In an embodiment in which the first reactor comprises a main reactor and an auxiliary one, the two groups of reactions may take place separately such that each reactor, main or auxiliary, contains only one type of these two catalysts, and the main and auxiliary reactors may be arranged in sequence, alternating, in parallel or in combined arrangements.

In the case that this first reactor comprises a main reactor and an auxiliary reactor to carry out the two groups of reactions and both the main reactor and the auxiliary one contain catalysts C1 and C2 mixed together, these reactors, main and auxiliary, may also be arranged in sequence, alternating, in parallel or in a combined manner.

In a second phase, the products resulting from the first phase, typically dimethyl ether and methanol, enter the second reactor of the device, wherein oxygen is added and they come into contact with catalyst C3 which favors the production of formaldehyde via the partial oxidation of part of the dimethyl ether or the methanol, via the following reactions: $CH_3OH+\frac{1}{2}O_2 \rightarrow CH_2O+H_2O$ y $CH_3OCH_3+O_2 \rightarrow 2CH_2O+H_2O$; they also favor the reaction $2CH_3OH \rightarrow CH_3OCH_3+H_2O$, producing dimethyl ether as a minority product.

If both products enter this second reactor, side reactions take place such as the following: $CH_3OCH_3 + H_2O \rightarrow 2CH_2O + 2H_2$, thus producing more formaldehyde and leaving as main by-products the excess water that did not react and hydrogen.

The preferred catalysts for these reactions, which we shall call C3, are based on at least two metals or compounds of the group: aluminum oxide, molybdenum oxide, vanadium and iron.

The residual water, a by-product of the third group of reactions that occur within the second reactor, condenses preferably at the end of this reactor or in a separate condenser and is extracted from the process before the products that circulate through it are discharged into the third reactor, preferably at a pressure and temperature not above those at which they exit the second reactor, in order to initiate the fourth and last group of reactions that will produce the multifunctional product.

During the fourth group of reactions, the molecules of aldehyde are incorporated to the dimethyl ether molecules via aldol reactions in order to reinforce the aldehyde content of the formulation of the multifunctional product, via which process, in this product, its volatility, flashpoint, vapor pressure and energy content can be adjusted according to the specific needs of the market in which it will be sold.

The third reactor is where the main intermediate products, dimethyl ether and formaldehyde, together with any unconverted synthesis gas and some minority by-products, are subjected to reactive distillation and come in contact with at least one type of strongly acidic catalyst, where the preferred one is an ion exchange resin which we shall call C4.

In the third reactor the optional additive may be incorporated, preferably comprising an amine to alkalinize and modify the pH of the multifunctional product, in order to prevent the reversal of the reactions of this group and to permanently sensitize the multifunctional product to detonation when used in internal combustion engines.

Regarding the amine referred to in the previous paragraph, the preferred one is ethylene diamine and the second preferred one is 2-dimethylaminoethylazide, and preferably this optional additive may be incorporated to the process diluted in at least one group of diluents of the following group: i) an alcohol with 1 to 4 carbon atoms doped with nitromethane and ii) dibutyl ether doped with propylene glycol monomethyl ether.

The multifunctional product in conjunction with part of the unconverted synthesis gas and minority by-products then exit the device so that they can be partially or totally separated by means of a fractional distillation.

With respect to the optional additive, this comprises preferably at least one amine wherein the preferred one is ethylenediamine and the second preferred one is 2-dimethylaminoethylazide.

When used for combustion, this optional additive may be diluted in an alcohol with 1 to 4 carbon atoms doped with nitromethane and/or diluted in dibutyl ether doped with propylene glycol monomethyl ether in order to increase the sensitivity to detonation provided to the multifunctional product by the amine.

One of the characteristics of this process is that between the first and second phase the pressure of the products resulting from the first phase is reduced, preferably by two-thirds, and the excess of pressure between the first and the second phase is used to increase the pressure of the products between the third and fourth phase.

In addition, the products from the first and second phase provide heat for the third reactor, to the raw materials entering the device or to the optional additive that enters the device via the additive injector.

To achieve this, the device has means to recover the heat and pressure.

The recovery of pressure and heat makes the process largely self-sufficient energetically.

2. Regarding the Device:

Regarding the device, and notwithstanding the above, it comprises at least three reactors connected in sequence wherein at least three of the four groups of main reactions occur, so that it can be used continuously and allowing the intermediate products to pass from one to the other without requiring storage outside the process.

Of these three reactors, at least one first reactor, which may comprise a main reactor and an auxiliary one, is for the first two groups of reactions; at least one second reactor is for the third group of reactions; and at least one third reactor is for the fourth group of reactions.

The first reactor contains at least one catalyst from amongst C1 and C2, the second reactor contains catalyst C3 and the third reactor contains catalyst C4.

All these reactors comprise a pipe bank within which the catalysts are found and through which the reagent products circulate.

The pipe bank for each reactor is covered by a jacket that rests on at least two seats, preferably four, and which may be disks/flanges.

In a preferred embodiment, with four disks/flanges, two at one end and two at the other end of the pipe bank, the outer disks/flanges serve as covers for the reactor. Between the inner disks/flanges and those serving as covers there are chambers that collect the products that enter or exit the pipe bank.

The outermost disks/flanges, those serving as covers for the reactor, are used to introduce or extract from the process certain materials such as raw materials, oxygen, water, additives or the end product.

The introduction or extraction of these materials is carried out through orifices that communicate with the inside and the outside of the aforementioned chambers.

Each reactor comprises at least two chambers, preferably each one on opposite ends thereof, in which said chambers comprise orifices to receive or discharge mainly the reagents and orifices communicated with the inside to receive or discharge the products that circulate within the pipes in the reactor.

The second and third reactor are communicated with oxygen and additive injectors, respectively.

The pipes of the pipe bank for each reactor are fastened to the disks/flanges adjacent to the chambers, preferably via welding, pressure or threads, and said disks/flanges have a through orifice for each pipe of the pipe bank.

The device comprises a direct means and an indirect means for transferring the heat from the main groups of exothermic reactions to the group of endothermic reactions, which may happen at the same time.

The different means that the device has for transferring this heat from the exothermic reactions to the endothermic reactions may be direct, indirect or a combination of both.

The direct means occurs via recirculation of the product resulting from the exothermic reactions of the first, second and third group of reactions, through the conduct in which the endothermic reactions occur, directly causing the heat exchange and transferring it to the endothermic reactions via said resulting product.

The indirect means occurs via recirculation of the product resulting from the exothermic reactions of the first, second and third group of reactions, through the conduct in which the endothermic reactions occur, indirectly causing the heat exchange and transferring it to the endothermic reactions via a fluid that does not chemically participate in the process.

We shall call combined means a means that uses the direct and indirect means to transfer heat. Any excess heat may be optionally transferred using any of the different means mentioned above: direct, indirect or combined.

3. Differentiating Factor of the End Product when Used as Fuel

The multifunctional product resulting from application of the optional additive, when used in internal combustion engines, has the characteristic of having a pH above 7, making it an alkaline product that is highly sensitive to detonation, which factors are positive and differentiating for its use as a component in fuels for internal combustion engines.

BRIEF DESCRIPTION OF FIG. 1

FIG. 1 shows a diagram of the process of the invention and the preferred catalysts that can be used, and should not be considered the only one but instead a mere descriptive example showing the device with a first reactor (1) comprising a main reactor (2) and an auxiliary reactor (3), a second reactor (4) and a third reactor (5).

In this case, the first group of reactions takes place in the main reactor (2) of the first reactor (1), the second group of reactions takes place in the auxiliary reactor (3) of the first reactor (1), the third group of reactions takes place in the second reactor (4), and the fourth group of reactions takes place in the third reactor (5).

Before the materials enter the first reactor they have passed through a compressor (6) and a heat exchanger (7).

An oxygen injector (8) is associated with the second reactor (4) and an injector of the optional additive (9) is associated with the third reactor (5).

After the third group of reactions and before the fourth group of reactions the residual water (10) is extracted from the process by the action of a condenser (13)

After the fourth group of reactions the multifunctional product (11) and the unconverted synthesis gas and any minority by-products (12) are extracted from the process.

Within the circuit there are at least two interconnections throttle/relief valves that are responsible for discharging any excess of product without affecting the environment and without the end production or quality of the multifunctional product being substantially affected.

These interconnections are a first interconnection (15) located between the main reactor (2) and the second reactor (4) and a second interconnection (14) located between the auxiliary reactor (3) and the third reactor (5).

DESCRIPTION OF AN EMBODIMENT OF THE INVENTION

We shall now describe an embodiment of the invention that is not unique but merely intended as an example.

The synthesis gas is compressed to 40 bar with the compressor (6) and it is then heated to 280° C. in the heat exchanger (7) in order to then enter the first reactor (1) via its main reactor (2) and its auxiliary reactor (3), which may be arranged in sequence or in parallel.

According to one possible embodiment, the synthesis gas enters in parallel to the main reactor (2) and the auxiliary reactor (3) of the first reactor (1). These reactors house catalysts C1 and C2 respectively, and both work at 280° C. and a pressure of 40 bar.

In the main reactor (2) of the first reactor (1) takes place the first group of reactions to produce mainly the methanol, which then enters the auxiliary reactor (3) together with the gas that did not react and other by-products from the first group of reactions. All the products that circulate through the main reactor (2) enter the auxiliary reactor (3) that contains catalyst C2, with the gas that did not react in the main reactor (2) to produce mainly dimethyl ether via the second group of reactions.

The dimethyl ether and the methanol, each in conjunction with their respective raw materials that did not react and the respective by-products derived from their respective reactions, such as carbon dioxide, methyl formate and carbonic acid, together with the oxygen and the optional additive injected from outside the device, all enter the second reactor (4) at the same temperature at which the products leave the auxiliary reactor (3) and at a reduced pressure so that, via the third group of reactions, the methanol may mainly be oxidized to formaldehyde, under the presence of catalyst C3. The oxygen is injected by an oxygen injector (8) comprising an orifice that communicates the outside with the inside of the second reactor (4) as shown in FIG. 1.

All products that circulate through the second reactor (4) are exposed to catalyst C3 to produce mainly formaldehyde and they pass through a condenser, preferably under pressure, to extract the residual water (10), preferably via a condenser (13) that is outside the device.

The products that exit the second reactor (4) and enter the third reactor (5) together with the optional additive that is injected from the outside by an additive injector (9), pass in contact with catalyst C4 in a temperature scenario of approximately 170° C. and a pressure of close to 20 bar, to generate the reactions of the fourth group, in which the multifunctional product (11) is mainly produced. This third reactor produces, as well as the multifunctional product, a minority or traces of: water, methanol, carbonic acid, formic acid, acetic acid, carbon dioxide, methyl formate and formaldehyde; other products also exit in gas form, from the raw material that was not converted, such as carbon monoxide, methane, hydrogen, oxygen and hydrocarbon traces, which we shall call minority by-products (12).

There are two interconnections with throttle/relief valves that are shown in FIG. 1. Both serve to discharge excess product without substantially affecting the production or end quality of the MULTIFUNCTIONAL product.

The interconnections are a first interconnection (15) from the main reactor (2) to the second reactor (4) and a second interconnection (14) from the auxiliary reactor (3) to the third reactor (5)

Whilst the different groups of reactions occur, the products from the first reactor (1), comprising its main (2) and auxiliary (3) reactors and from the second reactor (4) provide heat to the third reactor (5) indirectly via a non-volatile liquid that circulates between the jacket and the pipe bank containing the reactors, using a heat exchange, and the excess heat can optionally be applied to the raw materials entering the device and to the optional additive that may enter the device via the additive injector (9).

Finally, if so desired, the multifunctional product (11) that exits the third reactor (5) may be separated into its different components via a distillation, where fractional distillation is preferred.

The liquid or gas products that exit reactor R4 together with the polyoxymethylene dimethyl ethers, may optionally be recirculated and serve as a raw material for a gasification process for the production of synthesis gas.

In another example of an embodiment of the invention, the synthesis gas is compressed to 40 bar with the compressor (6) and is then heated to 280° C. in the heat exchanger (7) to then enter the main reactor (2) and the auxiliary reactor (3) which may be arranged in sequence or in parallel, where in the main reactor this synthesis gas comes in contact with catalyst C1 and in the auxiliary reactor (3) it comes in contact with catalyst C2. As a result a group of reactions occurs in each reactor wherein the end products of the main reactor and the auxiliary reactor are mainly methanol and dimethyl ether respectively, obtaining a weight conversion of more than 40% of the synthesis gas used.

The products of the main reactor (2) and the auxiliary reactor (3) where in the main reactor (2) the first group of reactions occurs and methanol is produced and where in the auxiliary reactor (3) the second group of reactions occurs and dimethyl ether is produced, all enter the second reactor (4) at a temperature and pressure no greater than those of the main reactor and the auxiliary reactor and they come in contact with catalyst C3 which favors the partial oxidation of the methanol and the dimethyl ether into formaldehyde, therefore generating liquid by-products, mainly: water, carbon dioxide, methyl formate, carbonic acid and methanol. Also present during this oxidation process are the gaseous by-products of the synthesis gas and part of the synthesis gas that did not react in the main (2) and auxiliary (3) reactors, mainly: hydrogen, carbon monoxide, carbon dioxide and nitrogen infiltrated with oxygen and raw materials.

The products of the main (2) and auxiliary (3) reactors both exit at 280° C. and 34 bar of pressure, which is preferably reduced to 12 bar, and then enter the second reactor (4) that houses the catalyst C3 and either pure oxygen or a compound containing oxygen is added with an oxygen injector (8).

In this second reactor (4) the methanol oxidizes almost entirely to formaldehyde, producing water as a by-product; part of the dimethyl ether also oxidizes in a lower proportion to formaldehyde, producing water as a by-product.

At the end of the second reactor (4) all the products circulating pass through a condenser (13) that is preferably on the end of the second reactor (4), although it could be external, so that mainly the residual water (10) produced as a by-product in the second reactor (4) condenses and can be extracted from the productive system.

The products coming out of the condenser apart from those extracted from the productive system, together with the optional additive, enter the third reactor (5) that contains catalyst C4 which is at a pressure of close to 20 bar and a temperature of 175° C., and produces the full group of reactions at mainly produce the multifunctional product with a conversion of the synthesis gas of more than 40%.

The end products exit at approximately 175° C. and 17 bar of pressure, and the conversion of the synthesis gas to the multifunctional product, by weight, is of approximately 40%, and at most 10% is methanol and at most 8% is other minority liquid by-products (12). The remaining percentage is of products that were not converted to the multifunctional product and exit as gases, together with those that did not manage to react and which are separated from the multifunctional product by cooling.

It is then convenient to separate the polyoxymethylene dimethyl ether from the undesired liquid by-products carried with the multifunctional product, wherein the liquid by-products separated together with the other gas products that exit from the third reactor may optionally be used in the production process for synthesis gas, in preheating raw materials and optional additives.

The invention claimed is:

1. A device, comprising:
   a first, second, and third reactor arranged in sequence,
   wherein the first reactor comprises a first plurality of pipes configured to hold first and second catalysts and contained within a first cover, wherein a first set of supports join the first plurality of pipes and the first cover, the first reactor further comprises a first set of at least two chambers in communication with an exterior of the first reactor,
   wherein the second reactor comprises a second plurality of pipes configured to hold a third catalyst and contained within a second cover, wherein a second set of supports join the second plurality of pipes and the second cover, the second reactor further comprises a second set of at least two chambers in communication with an exterior of the second reactor,
   wherein the third reactor comprises a third plurality of pipes configured to hold a fourth catalyst and contained within a third cover, wherein a third set of supports join the third plurality of pipes and the third cover, the third reactor further comprises a third set of at least two chambers in communication with an exterior of the third reactor;
   at least one compressor and at least two condensers;
   means to transfer heat from one reactor to another according to their requirements;
   means to collect or apply heat to the raw material entering the process;
   means for recovering pressure; and
   means for measuring, automating and controlling flow, temperature and pressure of the first, second, and third reactors.

2. The device according to claim 1, wherein the first reactor comprises a main reactor and an auxiliary reactor arranged in sequence, alternating or in parallel.

3. The device according to claim 1, wherein the first and second catalysts comprise at least one of $CuO/ZnO/Al_2O_3$ and aluminum oxide, the third catalyst comprises at least one of aluminum oxide, molybdenum, vanadium and iron, and the fourth catalyst comprises a strong acid.

4. The device according to claim 2, wherein the main reactor contains the first catalyst and the auxiliary reactor contains the second catalyst.

5. The device according to claim 1, wherein the first reactor contains the first and second catalysts mixed together.

6. The device according to claim 1, wherein the first cover is a first jacket and the first set of supports comprise a first plurality of flange disks comprising through holes, wherein the second cover is a second jacket and the second set of supports comprise a second plurality of flange disks comprising through holes, wherein the third cover is a third jacket and the third set of supports comprise a third plurality of flange disks comprising through holes.

7. The device according to claim 1, wherein the first chamber is in fluid communication with the first set of pipes, the second chamber is in fluid communication with the second set of pipes, and the third chamber is in fluid communication with the third set of pipes.

8. The device according to claim 1, wherein the second and third reactor are each in fluid communication with gas injectors.

* * * * *